(12) United States Patent
Jadav et al.

(10) Patent No.: US 6,506,940 B1
(45) Date of Patent: Jan. 14, 2003

(54) PROCESS FOR CONVERTING STEREOISOMERS OF SERTRALINE INTO SERTRALINE

(75) Inventors: Kanaksinh J. Jadav, Gujarat; Trinadha Rao Chitturi, Andhra Pradesh; Rajamannar Thennati, Tamil Nadu, all of (IN)

(73) Assignee: Sun Pharmaceuticals Industries Ltd., Mumbai (IN)

( * ) Notice: Subject to any disclaimer, the term of this patent is extended or adjusted under 35 U.S.C. 154(b) by 0 days.

(21) Appl. No.: 09/709,812

(22) Filed: Nov. 10, 2000

(51) Int. Cl.⁷ .................. C07C 211/00; C07B 57/00
(52) U.S. Cl. .................. 564/304; 564/308; 564/415
(58) Field of Search ................... 564/308, 415, 564/304

(56) References Cited

U.S. PATENT DOCUMENTS

| | | |
|---|---|---|
| 4,536,518 A | 8/1985 | Welch, Jr. et al. |
| 4,556,676 A | 12/1985 | Welch, Jr. et al. |
| 4,777,288 A | 10/1988 | Quallich et al. |
| 4,839,104 A | 6/1989 | Quallich et al. |
| 4,855,500 A | 8/1989 | Spavins |
| 5,082,970 A | 1/1992 | Braish |
| 5,196,607 A | 3/1993 | Quallich |
| 5,466,880 A | 11/1995 | Quallich |

FOREIGN PATENT DOCUMENTS

| | | |
|---|---|---|
| WO | WO 95/15299 | 6/1995 |
| WO | WO 98/15516 | 4/1998 |
| WO | WO 98/27050 | 6/1998 |
| WO | WO 99/36394 | 7/1999 |
| WO | WO 99/55686 | 11/1999 |

OTHER PUBLICATIONS

"Synthesis of 7–3H–(1S, 4S)–4–(3,4–dichlorophenyl)–1,2,3,4–tetrahydro–N–methyl–1–naphthalenamine hydrochloride (7–3H–Sertaline)," Willard M. Welch et al., . . . *Labelled Compounds and Radiopharmaceuticals*, vol. XXXIII No. 2, Sep. 1992, pp. 134–136, 138–14.

"Efficient Enantioselective Synthesis of Sertaline, a Potent Antidepressant, via a Novel Intramolecular Nucleophilic Addition to Imine," Cheng–yi Chen et al., *Organic Letters*, vol. 1, No. 2, 1999, pp. 293–294.

"Synthesis of 4(S)–(3,4–Dichlorophenyl)–3,4–dihydro–1(2H)–naphthalenone by SN2 Cuprate Displacement of an Activated Chiral Benzylic Alcohol," George J. Quallich et al., *Tetrahedron*, vol. 48, No. 47, 1992, pp. 10239–10248.

*Primary Examiner*—Samuel Barts
(74) *Attorney, Agent, or Firm*—Proskauer Rose LLP

(57) ABSTRACT

A process for converting the cis (1R, 4R), trans (1S, 4R), and trans (1R, 4S) stereoisomers of sertraline into sertraline comprises, starting with an initial reaction mixture which contains at least one of these stereoisomers, converting the sertraline stereoisomers into an imine form of sertraline. The imine form of sertraline is then reduced so that sertraline and at least one sertraline stereoisomer byproduct is produced in the reaction mixture. The sertraline is then recovered from the reaction mixture, e.g., by fractional crystallization (followed by resolution of sertraline from the cis (1R, 4R) stereoisomer, if necessary). The reaction mixture is then recycled through the same steps so that sertraline is produced from its stereoisomers in an asymptotic yield.

32 Claims, No Drawings

PROCESS FOR CONVERTING STEREOISOMERS OF SERTRALINE INTO SERTRALINE

INTRODUCTION

The present invention relates to a novel process for the conversion of (1R,4R) N-methyl-4-(3,4-dichlorophenyl)-3,4-dihydro-1(2H)-naphthaleneamine of formula 2, hereinafter referred to as cis (1R,4R) isomer, or trans (1S,4R), isomer of formula 3, or trans (1R,4S) isomer of formula 4, or mixtures thereof, to (1S,4S) N-methyl-4-(3,4-dichlorophenyl)-3,4-dihydro-1,2,3,4-tetrahydro-1-naphthaleneamine of formula 1, commonly known as sertraline (INN Name).

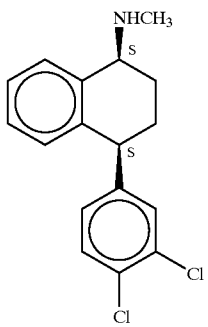

1

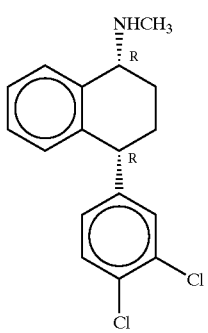

2

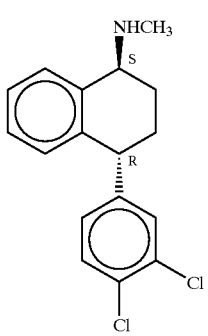

3

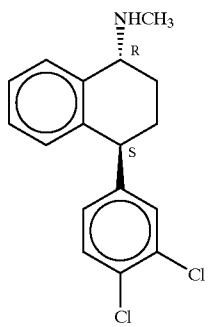

4

These aforesaid isomers of formulas 2, 3 and 4 are undesired stereoisomers of sertraline of formula 1, and are invariably co-produced during the manufacture of this drug by known processes such as that disclosed in U.S. Pat. No. 4,536,518, which is incorporated herein by reference. More particularly, the present invention relates to a novel process for recycling the undesired stercoisomers, both the trans isomers as well as the cis (1R,4R) isomer, to obtain sertraline in asymptotic amounts through an iterative process. Sertraline hydrochloride (commonly known as Zoloft®) is an important drug useful in the treatment of depression, obsessive-compulsive disorder and panic disorder.

BACKGROUND OF THE INVENTION

Sertraline has two chiral centres and hence has four stercoisomeric forms, namely, the (1R,4R), (1S,4S), (1R,4S), and (1S,4R) isomeric forms of setraline. Of these, the active stercoisomer for therapeutic purpose is the cis (1S,4S) isomer of formula 1.

U.S. Pat. Nos. 4,536,518 and 4,556,676, assigned to Pfizer, disclose a multi-step process for synthesis of pure (1S,4S) N-methyl-4-(3,4-dichlorophenyl)-3,4-dihydro-1(2H)-naphthaleneamine from 3,4-dichlorobenzophenone. The process proceeds via racemic 4-(3,4-dichlorophenyl)-3,4-dihydro-1(2H)-naphthalenone, a compound of formula 6.

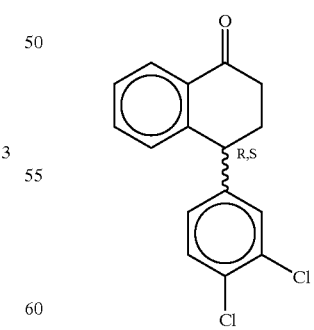

6

The ketone is condensed with methylamine to form a racemic imine mixture of formula 5c (shown below). The racemic imine is then reduced by means of catalytic hydrogenation or by the use of a metal hydride complex to N-methyl-4-(3,4-dichlorophenyl)-3,4-dihydro-1(2H)-naphthaleneamine, which is a racemic mixture of the cis and trans isomers. Trans isomers are separated from the cis isomers by fractional crystallization. Resolution of the separated cis racemate with optically active precipitant acid, such as D-(-)-mandelic acid in a classical manner, finally affords the desired cis-(1S,4S)-enantiomer (sertraline). The process has the disadvantage that large amounts of the undesired isomers of formulas 2, 3, and 4 are co-produced thereby lowering the overall yield of sertraline and increasing the production cost.

U.S. Pat. Nos. 4,777,288 and 4,839,104, assigned to Pfizer, disclose processes for the preparation of 4-(3,4-dichlorophenyl)-4-ketobutanoic acid in pure form and in high yield. The 4-(3,4-dichlorophenyl)-4-ketobutanoic acid is converted to racemic 4-(3,4-dichlorophenyl)-3,4-dihydro-1(2H)-naphthalenone, the compound of formula 6. Also, PCT International Publication No. WO 98/15516 discloses a process to prepare a compound of formula 6 in pure form by reacting α-naphthol and o-dichlorobenzene wherein the amount of by-product 4-(2,3-dichlorophenyl)-3,4-dihydro-1(2H)-naphthalenone is decreased below 1%. The racemic tetralone obtained by the processes of U.S. Pat. Nos. 4,777, 288; 4,839,104, and WO 98/15516 may be converted to sertraline by the process disclosed in U.S. Pat. Nos. 4,536, 518 and 4,556,676. The processes thus carry with them the prior art disadvantage in that large amounts of the undesired isomers of formulas 2, 3, and 4 are co-produced thereby lowering the overall yield of sertralille and increasing the production cost. U.S. Pat. No. 5,196,607 assigned to Pfizer discloses a multi-step process for preparing chiral (4S)-(3, 4-dichlorophenyl)-3,4-dihydro-1(2H)-napthalenone of formula 6a in pure form and high yield.

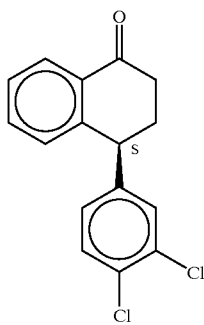

6a

Yet another method is described in U.S. Pat. No. 5,466, 880 whereby the chiral tetralone is prepared in an elaborate five-step process starting from 4-(3,4-dichlorophenyl)-4-ketobutanoic acid. Tetrahedron, 48(47), 10239 (1992), provides another method for preparing the chiral (4S) tetralone by reduction of 4-ketobutanoic acid ester with an asymmetric carbonyl reducing agent. The preparation of chiral tetralone allows for major improvement in the overall synthesis of sertraline in that the unwanted cis (1R,4R) isomer and trans (1S,4R) isomer are not co-produced when (4S) tetralone is converted to sertraline by methods described in U.S. Pat. Nos. 4,536,518; 4,556,676; 4,777,288; and 4,839,104.

PCT International Publication No. WO 95/15299 (Pfizer) describes a method for preparing chiral (4S)-(3,4-dichlorophenyl)-3,4-dihydro-1(2H)-napthalenone of formula 6a by asymmetric reduction of the corresponding racemic mixture with asymmetric ketone reducing agents, viz., chiral oxazaborolidine compounds to produce a mixture of cis and trans alcohols, from which the (4S) enantiomer is separated and oxidized to give the (4S) chiral tetralone.

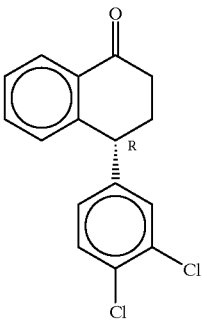

6b

The remaining mixtures of alcohols are oxidized to produce (4R) tetralone of formula 6b, which is then isomerized to racemic mixture of formula 6, with a base and recycled. The (4S) tetralone is then converted to sertraline by methods described in U.S. Pat. Nos. 4,536,518; 4,556,676; 4,777, 288; and 4,839,104.

The PCT International Publication No. WO 98/27050 discloses a three step process for the preparation of a mixture of sertraline and its cis (1R,4R) isomer using a novel N-oxide intermediate.

In a recent publication (Organic Lett., 1(2), 293 (1999) an enantioselective synthesis of sertraline using an anionic imine ring closure methodology is described starting from dichlorocinnamic acid.

In all the methods described above, eventual isomer separation is inevitable however, none of the methods discussed above provides methods for recycling the unwanted stereoisomers of sertraline. A process for recycling trans isomer of sertraline is described in U.S. Pat. No. 5,082,970. The process involves refluxing the trans isomer or a mixture with about an equal part by weight of the corresponding cis isomer with about 2 molar equivalents of a base such as potassium tert-butoxide for 48 hours in an inert polar solvent to afford a cis-trans mixture in a ratio of about 2:1. However, this method appears to have certain drawbacks in that i) an excess of base (2 mole equivalents) is used, ii) it requires 48 hours of reflux, and, most importantly, iii) the method is not exemplified with cis isomer containing (1R) center, which, incidentally, is the major unwanted isomer that is co-produced in equal amounts along with the desired cis-(1S) isomer. An experiment performed by the inventors herein on the cis (1R,4R) isomer, under the conditions described in the above-referred patent, did not result in isomerization at the C-1 center. This is understandable since the hydrogen at the C-1 position in sertraline isomers is not reactive under the conditions described, and hence is not susceptible to isomerization.

It is therefore, the object of the present invention to develop an alternate simple process whereby the unwanted isomers, both trans as well as the cis (1R,4R) isomer could be recycled to produce ultimately the desired cis (1S,4S) isomer in a simple manner which is commercially feasible.

SUMMARY OF THE INVENTION

The process of the present invention provides a method for converting the stereoisomers of sertraline into sertraline itself and comprises the steps of:

I. Converting cis (1R,4R) isomer of formula 2, or trans (IS,4R) isomer of formula 3, or mixtures thereof, to the corresponding (4R)-imine of formula 5a;
OR
Converting trans (1R,4S) isomer of formula 4 to the corresponding (4S)-imine of formula 5b;
OR
Converting a mixture of isomers of formulas 2 and 4, or a mixture of isomers of formulas 3 and 4, or a mixture of isomers of formula 2, 3 and 4, to the corresponding mixture of (4R)-said (4S)-imines of formula 5c;

II. Subjecting the (4R)-imine of formula 5a (if it has been produced in step I) to base catalyzed isomerization to produce a racemic imine mixture of formula 5c; and III. Reducing of the mixture of (4R)- and (4S)-imines of formula 5c to obtain a mixture of sertraline with stereoisomers of formula 2, 3 and 4;
OR
Reducing the (4S)-imine of formula 5b obtained in step I to obtain a mixture of sertraline and trans (1R,4S) isomer of formula 4.

Following step III, sertraline is separated from the reaction mixture, e.g., by fractional crystallization, and resolved, if necessary from the cis (1R, 4R) isomer. Thereafter or simultaneously, steps I, II, and III are repeated in an interative procedure so that sertraline is produced in an asymptotic yield.

The process described in this invention permits convenient recycling of the unwanted steroisomers of sertraline on a commercial scale as the entire process is simple and requires inexpensive raw materials.

The inventive process may also be described as a method for producing sertraline comprising:

(1) starting with an initial reaction mixture containing at least one sertralinc stereoisomer, converting said sertraline stereoisomer into an imine form of sertraline;

(2) reducing the imine form of sertraline into sertraline and at least one stereoisomer of sertraline;

(3) recovering sertraline from the reaction mixture; and (4) repeating steps (1), (2), and (3).

In one embodiment, the initial reaction mixture contains the cis (1R, 4R) stereoisomer of sertraline (formula 2) and/or the trans (1S, 4R) stereoisomer of sertraline (formula 3) which are first converted into the (4R)-imine (formula 5a) form of sertraline, which is then converted into a mixture of (4R)- and (4S)-imines of formula 5c before being converted into sertraline.

In another embodiment, the initial reaction mixture contains the trans (1R, 4S) stereoisomer of sertraline (formula 4) which is converted into the (4S)-imine of formula 5b before being converted into sertraline.

The process described herein may be illustrated in the following schematic diagram:

SCHEME 1

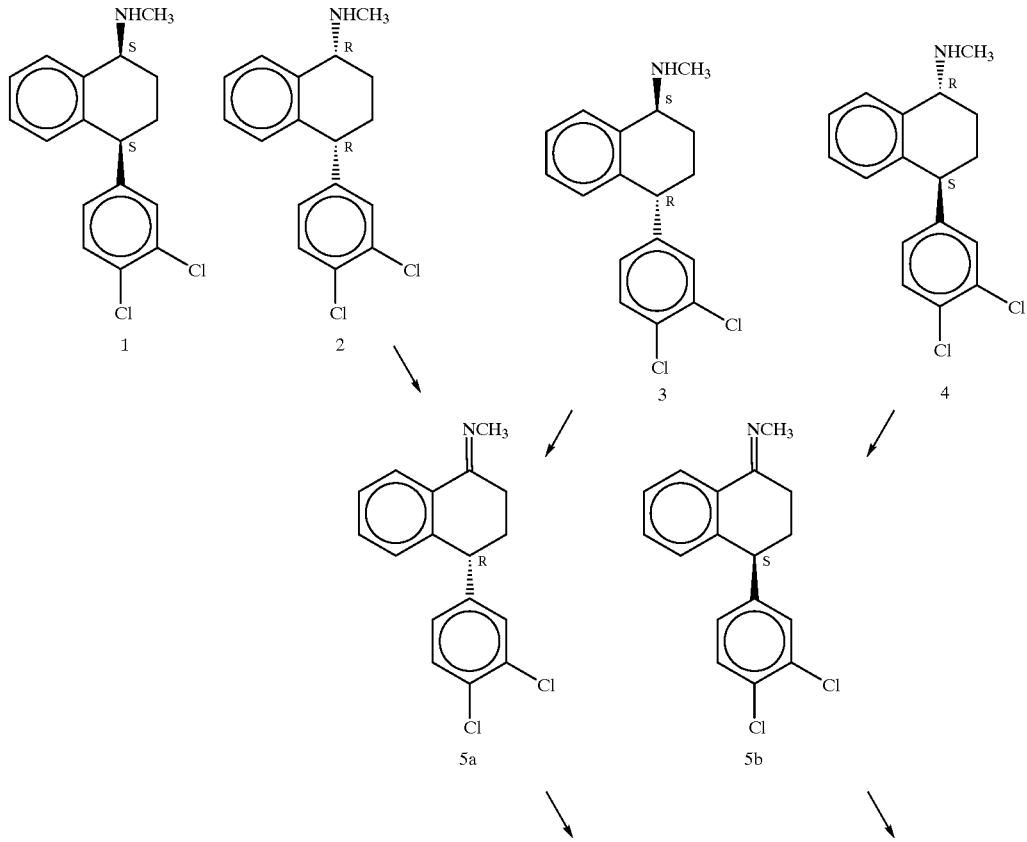

-continued

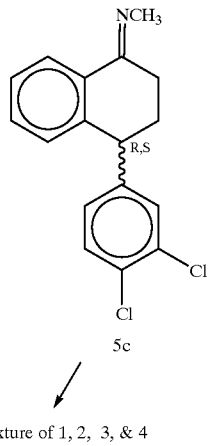

Mixture of 1 & 4

Mixture of 1, 2, 3, & 4

DETAILED DESCRIPTION OF THE INVENTION

The present invention relates to a process whereby the unwanted isomers, both trans isomers as well as the cis (1R,4R) isomer, of sertraline, are converted to the desired cis (1S,4S) isomer in a manner, which is simple, convenient, easily scaleable and commercially feasible. The inventive process differs from prior art methods of producing sertraline in that it proceeds by converting unwanted stereoisomers of sertraline into sertraline. The unwanted stereoisomers are first converted into an imine form of sertraline which eliminates the chirality at the C-1 position. The imine formed is stable and does not hydrolyze to ketone under the conditions of the present invention. This step is quite useful in comparison to prior art methods because it obviates the need to convert a ketone into an imine (when ketone is one of the intermediates produced). Once the imine is formed, it is then necessary to isomerize the C-4 position since the (4R) components are the major unwanted stereoisomers in the starting mixture. Isomerization is achieved under base catalyzed conditions in a very facile manner, a process hitherto unreported.

Thus, the process of the present invention is illustrated in Scheme I and comprises the steps of:

I. Converting cis (1R,4R) isomer of formula 2, or trans (1S,4R) isomer of formula 3, or mixtures thereof, to the corresponding (4R)-imine of formula 5a;

OR

Converting trans (1R,4S) isomer of formula 4 to the corresponding (4S)-imine of formula 5b;

OR

Converting a mixture of isomers of formula 2 and 4, or a mixture of isomers of formula 3 and 4, or a mixture of isomers of formula 2, 3 and 4, to the corresponding mixture of (4R)- and (4S)-imines of formula 5c;

II. If the (4R)-imine of formula 5a has been produced in Step I, subjecting the (4R)-imine of formula 5a to base catalyzed isomerization to produce a racemic imine mixture of formula 5c;

III. Reducing the mixture of (4R)- and (4S)-imines of formula 5c to obtain a mixture of sertraline with isomers of formula 2, 3, and 4;

OR

If the (4S)-imine of formula 5b has been produced in Step I, reducing the (4S)-imine of formula 5b to obtain a mixture of sertraline and trans (1R,4S) isomer of formula 4.

Following these steps, sertraline of formula 1 is separated from the reaction mixture and, if necessary, resolved from the cis (1R, 4R) isomer. The unwanted byproduct isomers are recycled through the same steps to produce setraline in asymptotic yield.

According to the process of the present invention, in step I of the process cis (1R,4R) isomer of formula 2, or trans (1S,4R) isomer of formula 3, or mixtures thereof is/are converted to the corresponding (4R)-imine of formula 5a; or trans (1R,4S) isomer of formula 4 is converted to the corresponding (4S)-imine of formula 5b; or a mixture of stereoisomers of formulas 2 and 4, or a mixture of stereoisomers of formulas 3 and 4, or a mixture of stereoisomers of formulas 2, 3 and 4, are converted to a mixture of (4R)- and (4S)-imines of formula 5c. The conversion may be carried out by oxidation in the presence of a base using a halogen ion generating reagent such as N-haloamides, N-haloimides and N-halohydantoins. Step I of the process is preferably carried out by oxidation using a hypohalite. The preferred halogen ion generating reagents are N-bromosuccinimide and N-chlorosuccinimide. The hypohalite may be added to the reaction mixture or generated in-situ by reaction of a halogen with a base preferably in a protic solvent. Examples of bases that may be used include alkali metal hydroxides such as LiOH, NaOH, KOH, CsOH; and alkali metal carbonates such as $Li_2CO_3$, $Na_2CO_3$, $K_2CO_3$. The preferred bases that can be employed are alkali metal hydroxides such as LiOH, NaOH, KOH, CsOH. The most preferred is NaOH. The protic solvents that may be used include aqueous or alcoholic solvent(s) or mixtures thereof. The most preferred solvent is methanol.

According to the process of the present invention, in step II of the process, the (4R)-imine of formula 5a (if it has been produced in step I) is subjected to base catalyzed isomerization to yield a racemic imine mixture of formula 5c. Base catalyzed isomerization may be carried out by using non-nucleophilic organic bases. Examples of non-nucleophilic organic bases that may be used include metal alkoxides, metal amides, dimsyl or trityl metal salts, and the like. Preferably, the non-nucleophilic organic base is a metal alkoxide; more preferably an alkali metal alkoxide; most preferably potassium tert-butoxide. Preferably, the alkali metal alkoxide is used in a mole ratio of about 5% to about 20%, preferably 10%, with respect to the imine. The solvent for the isomerization reaction is an aprotic solvent that may include ethers, acyclic or cyclic, such as diisopropyl ether, tert-butyl methyl ether, tetrahydrofuran, 1,4-dioxane, and the like; aromatic hydrocarbons such as toluene, xylenes, and the like. The preferred solvents are ethers such as tetrahydrofuran and 1,4-dioxane. The most preferred solvent is tetrahydrofuran. The temperature for the isomerization reaction may range from ambient to about 140° C., preferably about 70° C. to about 75° C. The reaction time ranges from 1 to 10 hours, preferably about 2 to about 3 hours. After the reaction is completed, the reaction mixture is concentrated and degassed, an appropriate quantity of water is added, and the isomerized racemic imine is isolated by filtration. In the case where the solvent used for the reaction is immiscible with water, the reaction mixture is simply washed with an appropriate quantity of water, and the solvent is degassed to recover the isomerized racemic imine.

According to the process of the present invention, step III comprises reduction of the mixture of (4R)- and (4S)-imines of formula 5c to obtain a mixture of sertraline with stereoisomers of formulas 2, 3, and 4; or reduction of (4S)-imine of formula 5b (if it was obtained in step I) to obtain a mixture of sertraline and trans (1R,4S) isomer of formula 4. Reduction may be achieved by the use of a metal hydride complex or by means of catalytic hydrogenation. Preferably, the mixture of (4R)- and (4S)-imine of formula 5c or the (4S)-imine of formula 5b is reduced by catalytic hydrogenation. Catalytic hydrogenation results in a mixture of stereoisomers wherein the cis isomer(s) are present in amounts greater than the trans isomer(s). More preferably, the imine(s) is/are catalytically hydrogenated to get predominantly the cis isomers, along with minor quantity of trans isomers. The catalytic hydrogenation is preferably carried out in protic solvents such as primary, secondary, tertiary alcohols or mixtures thereof. Examples of the hydrogenation catalysts that may be used include Raney Nickel or precious metal promoters such as platinum or palladium on supports such as carbon, graphite, calcium carbonate, and the like. The catalytic hydrogenation may also be carried out using copper containing catalysts such as copper chromite in aprotic solvents, particularly ethers such as tetrahydrofuran.

Separation of the cis and trans isomers and subsequent resolution of cis (1R,4R) and (1S,4S) stereoisomers, or of trans (1R,4R) and (1S,4R) stereoisomers as their hydrochlorides, is carried out by methods well known to those skilled in the art and heretofore described in the literature, e.g., cis isomers may be separated from a mixture of cis and trans isomers by fractional crystallization or chromatography; and resolution of the cis (1S,4S) and cis (1R,4R) isomers may be achieved by treating a solution of cis-racemate free base with an optically active precipitant acid such as D-(−)-mandelic acid and precipitating the less soluble diastereomeric salt.

According to a preferred embodiment of the present invention, the undesired isomers of sertraline are recycled by a process comprising the following steps:
a. Isolation of a mixture of sertraline and cis (1R,4R) isomer from the mixture of sertraline with stereoisomers of formulas 2, 3, and 4 obtained in step III; followed optionally by repetition of steps I, II and III, or by repetition of steps I and III on the mixture of trans (1R,4S) and trans (1S,4R) isomers;
OR
Isolation of sertraline from the mixture of sertraline and trans (1R,4S) isomer of formula 4 obtained in step III; followed optionally by repetition of steps I and III on the trans (1R,4S) isomer;
b. Resolution of the mixture of sertraline and cis (1R,4R) isomer of formula 2 obtained in step a; followed optionally by repetition of steps I, II, and III on the cis (1R,4R) isomer; and
c. Resolution of the mixture of trans (1R,4S) and trans (1S,4R) isomers obtained in step a; followed optionally by repetition of steps I, II and III on the trans (1S,4R) isomer and repetition of steps I and III on the trans (1R,4S) isomer.

The process described in this invention, thus permits convenient recycling of the unwanted steroisomers of sertraline to the desired (1S,4S) sertraline in asymptotic amounts through iteration. The process described is feasible on a commercial scale in view of the fact that the operations involved are simple and the raw materials required are not expensive.

The invention is illustrated but not restricted by the description in the following examples.

EXAMPLES

Example 1

Preparation of (R)-N-[4-(3,4-dichlorophenyl)-3,4-dihyro-1-(2H)-naphthalenylidene]methanamine (formula 5a) from (1R,4R)-N-methyl-4-(3,4-dichlorophenyl)-1,2,3,4-tetrahydro-1-naphthalenamine (formula 2)

(1R,4R)-N-methyl-4-(3,4-dichlorophenyl)-1,2,3,4-tetrahydro-1-naphthalenamine 100 g (0.326 mol.) was dissolved in 900 ml methanol and 78.4 g (1.96 mol.) NaOH was added to it and cooled to 30–35° C. To the cooled solution was added 18.5 ml (0.358 mol.) bromine during 2 hour under stirring while maintaining temperature in the range of 35–40° C. using an ice water bath. After stirring for 30 minutes at 30–35° C., the solid formed was separated by filtration and washed with 2×100 ml methanol. The product was then suspended in 500 ml water, stirred for 15 minutes at 25–30° C. and filtered. The product was washed with 2×250 ml water and allowed to suck dry. The product was finally dried at 55–60° C. under vacuum, the yield 78.7 g (78.18%, $[\alpha]_D^{25}$ (1% in chloroform) ranges from=−72° to −76°).

Example 2

Preparation of (R)-N-[4-(3,4-dichlorophenyl)-3,4-dihyro-1-(2H)-naphthalenylidene]methanamine (formula 5a) from (1R,4R)-N-methyl-4-(3,4-dichlorophenyl)-1,2,3,4-tetrahydro-1-naphthalenamine (formula 2) hydrochloride The procedure described in Example-1 was repeated using (1R,4R)-N-methyl-4-(3,4-dichlorophenyl)-1,2,3,4-tetrahydro-1-naphthalenamine hydrochloride, 10 g (0.029 mol.), except that sodium hydroxide was taken in the mole ratio 7:1 instead of 6:1 with respect to the amino compound, i.e, 8.17 g (0.204 mol.). The product was isolated in the same manner as in Example 1.

Example 3

Racemization of (R)-N-[4-(3,4-dichlorophenyl)-3,4-dihyro-1-(2H)-naphthalenylidene]methanamine (formula 5a)

A suspension of 100 g (0.329 mol.) (R)-N-[4-(3,4-dichlorophenyl)-3,4-dihyro-1-(2H)-naphthalenylidene]methanamine and 3.7 g (0.0329 mol.) potassium tertiary butoxide in 300 ml tetrahydrofuran was heated to 70–72° C. and stirred for 2 hours. A sample (2 ml) of the reaction mixture was withdrawn for checking specific rotation. If specific rotation was 0±2°, the solvent was distilled out at atmospheric pressure and the mixture cooled to 30–35° C. Water 500 ml was added to the residual material and stirred for 15 min. The product was filtered, washed successively with 3×100 ml water and 2×100 ml isopropyl ether and sucked dry. The product was finally dried at 55–60° C. under vacuum to yield 83 g (83%).

Example 4

Preparation of racemic (R),(S)-N-[4-(3,4-dichlorophenyl)-3, 4-dihyro-1-(2H)-naphthalenylidene]methanamine (formula 5c) from racemic mixture containing (1S,4R) and (1R, 4S)-N-methyl-4-(3,4-dichlorophenyl)-1,2,3,4-tetrahydro-1-naphthalenamines (formulas 3 and 4)

The same procedure as in Example-1 was followed using a racemic mixture containing (1R,4S), (1S,4R)-N-methyl-4-(3,4-dichlorophenyl)-1,2,3,4-tetrahydro-1-naphthalenamine, 25 g (0.082 mol.). The product obtained was identical to that obtained in Example-3.

Example 5

Preparation of racemic (R),(S)-N-[4-(3,4-dichlorophenyl)-3,4-dihyro-1-(2H)-naphthalenylidene] methanamine (formula 5c) from racemic mixture containing (1S,4R) and (1R, 4S)-N-methyl-4-(3,4-dichlorophenyl)-1,2,3,4-tetrahydro-1-naphthalenamine (formulas 3 and 4) hydrochlorides The same procedure as in Example-2 was followed using a racemic mixture containing (1R,4S), (1S,4R)-N-methyl-4-(3,4-dichlorophenyl)-1,2,3,4-tetrahydro-1-naphthalenamine, 28 g (0.082 mol.). The product obtained was identical to that obtained in Example-3.

Example 6

Conversion of mixture of (R) and (S)-N-[4-(3,4-dichlorophenyl)-3,4-dihyro-1-(2H)-naphthalenylidenel] methanamines (formula 5c) to (1S,4S) and (1R, 4R)-sertraline (formulas 1 and 2) hydrochlorides (cis-sertraline hydrochloride) mixture The isomerized imine from Example-5 83 g was taken in 400 ml 2-propanol, 4.0 g of Raney-Nickel was added and hydrogenated at a pressure of 4.5–5.0 kg/cm$^2$ and 70–80° C. until there was no further consumption of hydrogen. The reaction mass was filtered and the catalyst washed with 200 ml 2-propanol. From combined filtrate and washings, 200 ml of 2-propanol was distilled out at 55–60° C. under reduced pressure and to the concentrate was added 36.5 ml (0.44 mol.) of conc. HCl. The mixture was stirred for 2 hrs at 30–35° C. and filtered. The separated solid was washed with 200 ml of 2-propanol. The product was then stirred with 400 ml methylene chloride, filtered, washed with 200 ml methylene chloride and then dried at 60–65° C. to yield (1R,4R) and (1S, 4S)-sertraline hydrochlorides. The yield was 61 g (68.72%).

While the invention has been described by reference to specific embodiments, this was for purposes of illustration only and should not be construed to limit the spirit or the scope of the invention.

What is claimed is:

1. A process for producing cis (1S,4S) sertraline comprising:
   (1) starting with an initial reaction mixture containing at least one sertraline stereoisomer, converting said sertraline stereoisomer into an imine form of sertraline;
   (2) reducing said imine form of sertraline into cis (1S,4S) sertraline and at least one byproduct, said byproduct also being a stereoisomer of sertraline;
   (3) recovering said cis (1S,4S) sertraline from said reaction mixture; and
   (4) repeating steps (1), (2), and (3).

2. The process of claim 1, wherein said sertraline stereoisomer is selected from the group consisting of cis (1R, 4R), trans (1S, 4R), and trans (1R, 4S) stercoisomers of sertraline, and mixtures thereof.

3. The process of claim 1 wherein said imine form of sertraline is selected from the group consisting of (4R)-imine and (4S)-imine forms of sertraline, and mixtures thereof.

4. The process of claim 1, wherein the initial reaction mixture contains cis (1R, 4R) or trans (1S, 4R) stereoisomers of sertraline, or mixtures thereof, which are converted to (4R)-imine form of sertraline, which is then subjected to base catalyzed isomerization into a racemic mixture of (4R)- and (4S)-imine forms of sertraline.

5. The process of claim 1, wherein said imine form of sertraline comprises a racemic mixture of (4R)- and (4S)-imine forms of sertraline, which is reduced to a mixture of sertraline, cis (1R, 4R) sertraline, trans (1S, 4R) sertraline, and trans (1R, 4S) sertraline.

6. The process of claim 1, wherein said initial reaction mixture contains trans (1R, 4S) stereoisomer of sertraline which is converted into (4S)-imine form of sertraline.

7. The process of claim 1, wherein said imine form of sertraline comprises (4S)-imine form of sertraline which is reduced to a mixture of cis (1S,4S) sertraline and a trans (1R, 4S) stereoisomer of sertraline.

8. The process of claim 1, wherein said stereoisomer of sertraline in said initial reaction mixture is converted into said imine form of sertraline by oxidation with a hypohalite.

9. The process of claim 8, wherein said hypohalite is generated in situ in said reaction mixture by the reaction of a halogen with a base.

10. The process of claim 9, wherein said halogen is bromine or chlorine, said base is an alkali metal hydroxide or an alkali metal carbonate, which are reacted together in a protic solvent.

11. The process of claim 10, wherein said protic solvent is water, an alcohol, or mixtures thereof.

12. The process of claim 11, wherein said protic solvent is methanol.

13. The process of claim 10, wherein said alkali metal hydroxide is LiOH, NaOH, KOH, or CsOH.

14. The process of claim 10, wherein said alkali metal carbonate is Li$_2$CO$_3$, Na$_2$CO$_3$, or K$_2$CO.

15. The process of claim 1, wherein said stereoisomer of sertraline in said initial reaction mixture is converted to said imine form of sertraline by oxidation with a halogen ion generating reagent.

16. The process of claim 15, wherein said halogen ion generating reagent is N-haloamide, N-halomimide, or N-halohydantoin.

17. The process of claim 16, wherein said halogen ion generating reagent is N-bromosuccinimide or N-chlorosuccinimide.

18. The process of claim 1, wherein said initial reaction mixture contains cis (1R, 4R) or trans (1S, 4R) stereoisomers of sertraline, or mixtures thereof, which are converted to (4R)-imine form of sertraline, which is then subjected to base catalyzed isomerization to produce a racemic mixture of (4R)- and (4S)-imine form of sertraline, wherein the base catalyzed isomerization of the (4R)-imine form of sertraline is carried out using a non-nucleophilic organic base in an ether or an aromatic hydrocarbon solvent at a temperature from about ambient to about 140° C.

19. The process of claim 18, wherein said non-nucleophilic organic base is a metal alkoxide, a metal amide, or a dimsyl or trityl metal salt.

20. The process of claim 19, wherein said non-nucleophilic organic base is an alkali metal alkoxide.

21. The process of claim 20, wherein the alkali metal alkoxide is potassium tert-butoxide.

22. The process of claim 21, wherein the amount of alkali metal alkoxide comprises about 5 mole % to about 20 mole % of the imine form of sertraline.

23. The process of claim 18, wherein, said base is an alkali metal alkoxide and said solvent is tetrahydrofuran or 1,4-dioxane.

24. The process of claim 23, wherein said base is potassium tert-butoxide and said solvent is tetrahydrofuran.

25. The process of claim 24, wherein the potassium tert-butoxide is present in a mole ratio of about 5% to about 20% with respect to the imine form of sertraline.

26. The process of claim 25, wherein the base catalyzed isomerization is carried out at a temperature in the range of about 70° C. to about 75° C.

27. The process of claim 1, wherein the imine form of sertraline comprises a racemic mixture of (4R)- and 4(S)- imine forms of sertraline which is reduced by catalytic hydrogenation to obtain a mixture of cis (1S, 4S) sertraline, cis (1R, 4R), trans (1S, 4R), and trans (1R, 4S) stereoisomers of sertraline, and wherein the cis (1S, 4S) sertraline and the cis (1R, 4R) stercoisomer of sertraline are produced in greater amounts than the trans stereoisomers of sertraline.

28. The process of claim 27, wherein the catalytic hydrogenation is carried out in a protic solvent.

29. The process of claim 28, wherein said protic solvent is a primary, secondary or tertiary alcohol, or mixtures thereof.

30. The process of claim 29, wherein the solvent is 2-proponol and the catalytic hydrogenation in is carried out in the presence of Raney Nickel.

31. The process of claim 1, wherein the sertraline is recovered from said reaction mixture by fractional crystallization.

32. The process of claim 31, wherein the cis (1S, 4S) sertraline is recovered from said reaction mixture along with the cis (1R, 4R) stereoisomer, the process further comprising isolating the cis (1S, 4S) sertraline from the cis (1R, 4R) stereoisomer of sertraline.

* * * * *